US006902316B1

United States Patent
Pierce et al.

(10) Patent No.: US 6,902,316 B1
(45) Date of Patent: Jun. 7, 2005

(54) NON-INVASIVE CORROSION SENSOR

(75) Inventors: Christopher T. Pierce, Bedford, IN (US); Daniel S. Ellison, Bloomington, IN (US); Steve R. Turpen, Shoals, IN (US); Clayton A. Williams, Bedford, IN (US)

(73) Assignee: The United States of America as represented by the Secretary of the Navy, Washington, DC (US)

( * ) Notice: Subject to any disclaimer, the term of this patent is extended or adjusted under 35 U.S.C. 154(b) by 0 days.

(21) Appl. No.: 10/774,649

(22) Filed: Feb. 5, 2004

(51) Int. Cl.[7] .................. G01N 25/72; G01N 17/00
(52) U.S. Cl. ................ 374/7; 374/4; 374/45; 374/57; 374/5; 374/1
(58) Field of Search .............. 374/4, 7, 45, 57, 374/120, 129, 44, 1, 5

(56) References Cited

U.S. PATENT DOCUMENTS

| | | | |
|---|---|---|---|
| 4,647,220 A | | 3/1987 | Adams et al. |
| 4,780,664 A | * | 10/1988 | Ansuini et al. ............. 324/700 |
| 5,251,980 A | * | 10/1993 | Hiraoka et al. ................ 374/7 |
| 6,487,914 B1 | * | 12/2002 | Hodge ......................... 73/800 |
| 6,490,927 B2 | * | 12/2002 | Braunling et al. ............ 73/597 |
| 6,564,620 B1 | * | 5/2003 | Jaeger ........................... 73/86 |
| 6,579,005 B2 | * | 6/2003 | Ingallinera ................... 374/45 |
| 6,628,111 B2 | * | 9/2003 | Shapiro et al. ............ 324/71.2 |
| 6,712,502 B2 | * | 3/2004 | Zalameda et al. ............. 374/7 |
| 2003/0012254 A1 | * | 1/2003 | Park et al. .................... 374/45 |
| 2004/0189331 A1 | * | 9/2004 | Girshovich et al. ......... 324/694 |

OTHER PUBLICATIONS

Virginia Technologies, Inc., Test Data for Model ECI Embedded Corrosion Instrument, Sep. 19, 2000.
Dacco Sci, Inc., DSI In–Situ Corrosion Sensor, Mar. 19, 2003, located at www.daccosci.com.
G.M. Davis, C.M. Dacres, M.Shook, B.S. Wenner, Electrochemical In–Situ Sensors for Detecting Corrosion on Aging Aircraft, Apr. 25, 2000, located at www.daccosci.com.

* cited by examiner

*Primary Examiner*—Gail Verbitsky
*Assistant Examiner*—Madeline Gonzalez
(74) *Attorney, Agent, or Firm*—Mark O. Glut; NAVAIR, Naval Air Systems Command

(57) ABSTRACT

The non-invasive corrosion sensor includes a heat sink, at least two peltiers, a reference standard and a data acquisition device. Each peltier has a negative side and a positive side, and each peltier communicates with the heat sink such that the negative side of each peltier is maintained at a common temperature. The reference standard communicates with the positive side of one of the peltiers while the test piece communicates with the positive side of the other peltier; and the data acquisition devise is able to record and compare the differences in temperatures between the test piece and the reference standard. A higher temperature in the test piece than in the reference standard indicates the presence of corrosion. The differences in temperatures of the test piece and the reference standard are obtained via electrical currents in the peltiers.

11 Claims, 2 Drawing Sheets

NON-INVASIVE CORROSION SENSOR

STATEMENT OF GOVERNMENT INTEREST

Figure 1:
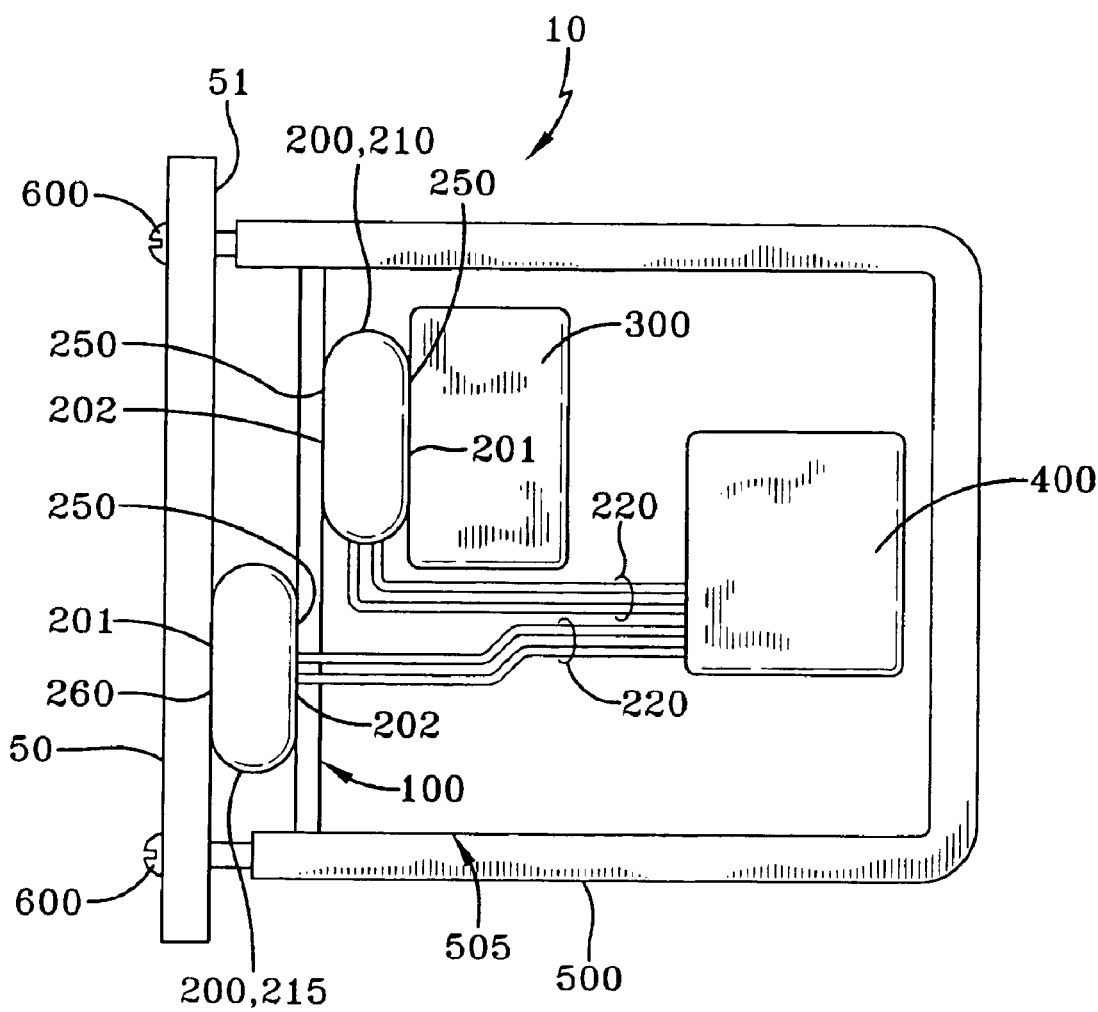

The invention described herein may be manufactured and used by or for the Government of the United States of America for governmental purposes without payment of any royalties thereon or therefor.

BACKGROUND

The present invention relates to a non-invasive corrosion sensor. More specifically, but without limitation, the present invention relates to a non-invasive corrosion sensor for detecting and measuring the rate of corrosion.

Current methods for detecting and measuring the rate of corrosion are non-quantitative, non-predictive and require visual observation of the surfaces. These methods often result in increased costs due to maintenance operations being performed prior to need or not soon enough. In either case the costs could be significantly reduced if maintenance could be performed at the most optimum time. This can only be accomplished through use of a method that will permit quantitative, continuous measurement of material surfaces not accessible during normal operations.

A commonly used method for detecting and measuring the rate of corrosion is visual inspection. To utilize this method the area must be accessible to viewing. Another method includes ultrasonic testing whereby sound waves detect changes in material properties (thickness and density). Additional methods are eddy current testing which detects changes in material/magnetic properties, and resistively testing which measures changes in a material's electrical resistance. All of these methods suffer from one or more of the above listed liabilities.

Thus, there is a need in the art to provide a method or mechanism that incorporates the listed benefits without the limitations inherent in present methods. For the foregoing reasons, there is a need for a non-invasive corrosion sensor.

SUMMARY

The present invention is directed to a non-invasive corrosion sensor. The non-invasive corrosion sensor includes a heat sink, at least two peltiers, a reference standard and a data acquisition device. Each peltier has a negative side and a positive side, and each peltier communicates with the heat sink such that the negative side of each peltier is maintained at a common temperature. The reference standard communicates with the positive side of one of the peltiers while the test piece communicates with the positive side of the other peltier; and the data acquisition device is able to record and compare the differences in temperatures between the test piece and the reference piece. A higher temperature in the test piece than in the reference standard indicates the presence of corrosion. The differences in temperatures of the test piece and the reference standard are obtained via electrical currents in the peltiers.

It is an object of the invention to provide a non-invasive corrosion sensor for detecting and measuring the rate of corrosion that is quantitative and predictive.

It is an object of the invention to provide a non-invasive corrosion sensor that does not require visual observation of the surfaces.

It is an object of the invention to provide a non-invasive corrosion sensor that does not require operators to perform a test or collect data.

DRAWINGS

Figure 2:
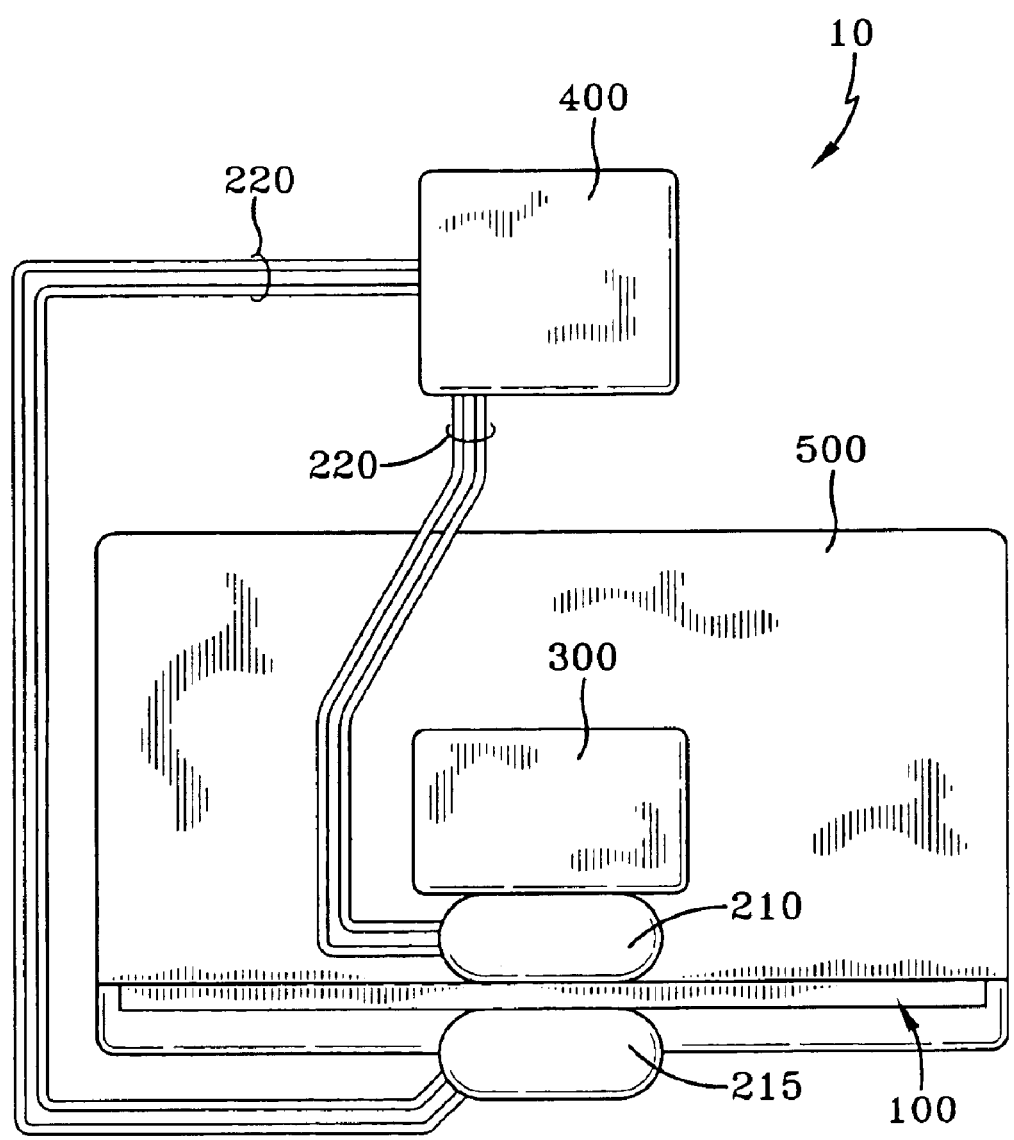

These and other features, aspects and advantages of the present invention will become better understood with reference to the following description and appended claims, and accompanying drawings wherein:

FIG. 1 is a side view of one of the embodiments of the non-invasive corrosion sensor, and, FIG. 2 is a side view of another one of the embodiments of the non-invasive corrosion sensor.

DESCRIPTION

The preferred embodiments of the present invention are illustrated by way of example in FIGS. 1 and 2. As seen in FIGS. 1 and 2, the non-invasive corrosion sensor 10 includes a heat sink 100, at least two peltiers 200, and a reference standard 300. Each peltier 200 may include a positive side 201 and a negative side 202. The peltiers 200 communicate with the heat sink 100 such that the negative side 202 of each of the peltiers 200 is maintained at a common temperature. The reference standard 300 communicates with the positive side 201 of one of the peltiers while the test piece 50 communicates with the positive side 201 of the other peltier 200. A data acquisition device 400 may be utilized to record and compare the differences in temperatures of the test piece 50 and the reference standard 300.

A heat sink 100 may be defined, but without limitation, as a material with high thermal conductivity used to equilibrate the temperatures on adjacent sides of the peltier 200. In the preferred embodiment of the invention the heat sink 100 is manufactured from aluminum.

A peltier 200 may be defined, but without limitation, as a thermo-electric device made of semiconductor material which heats or cools when an electric current is passed through the conductors. Conversely when the opposing surfaces of a peltier 200 are subjected to a temperature differential a measurable and calibratible current will be generated. This current can be converted to a microwatt heat load. As seen in FIGS. 1 and 2, the preferred embodiment of the invention includes two peltiers 200: a reference peltier 210 and a test piece peltier 215. The reference peltier 210 thermally communicates with the reference standard 300, while the test piece peltier 215 thermally communicates with the test piece 50. The negative side 202 of each peltier 200 is maintained at a common temperature through contact with the common heat sink 100. The opposing positive side 201 of the each peltier 200 is in contact with the reference standard 300 and the test piece 50 respectively.

A reference standard 300 may be defined, but without limitation, as a material identical to the test piece 50 (the material being monitored). In the preferred embodiment, the reference standard 300 is polished to remove all surface corrosion/contaminates and is sealed for protection.

The data acquisition device 400 may be defined, but without limitation, as a device capable of measuring and recording small electrical currents.

The non-invasive corrosion sensor 10 may also include an enclosure 500. The heat sink 100, the peltier(s) 200, and the reference standard 300 may be disposed within the enclosure 500. The preferred embodiment of the enclosure 500 is manufactured from polycarbonate. Polycarbonate may be defined, but without limitation, as a tough, highly impact resistant, corrosion resistant, non-conductive polymer. The interior of the enclosure 500 and its components may be environmentally sealed with flowable RTV (Room Temperature Vulcanizing) silicone coating 505. The preferred embodiment of the silicone coating is a one-part, flowable, solvent-free room temperature cure, which can be found under the brand name of Dow Corning® 3140 RTV Coating.

In the preferred embodiment of the sensor 10, the test piece peltier 215 is external to the enclosure 500. Each of the peltiers 200 may include peltier leads 220.

The enclosure 500 is designed to bolt into contact with the test piece 50. Twin peltier leads 220 from the reference peltier 210 and the test piece peltier 215 may protrude from the enclosure 500. Each negative side 202 of the two peltiers 200 is bonded to the heat sink 100 with thermal epoxy 250. The positive side 201 of the internal or reference peltier 210 is bonded to the reference standard 300 with thermal epoxy 250. Thermal epoxy 250 may be defined, but without limitation, as a two part epoxy which forms a permanent thermal bond. Thermal epoxy 250 may be, but without limitation, silver filled, aluminum oxide filled or aluminum nitride filled. The preferred thermal epoxy 250 may have a thermal conductivity of about 1.73 W/m-K, and may operate in temperatures of about −55 to about 125° C. The preferred thermal epoxy cures in about 1 hour at about 85° C. The preferred thermal epoxy is a two-part aluminum oxide filled epoxy TEC manufactured by Melcor. Thermal interface material, constructed of aluminum oxide with Adhesive Interface Pads, may be substituted for the thermal epoxy. The preferred embodiment of the thermal interface material may have a thermal conductivity of about 1.7 W/m-K and a maximum operating temperature of about 150° C. However, it is understood that any material that can bond, bind, fasten, or the like can be used.

In operation, the sensor 10 is fastened to the test piece 50 with stainless cap screws 600 or any other type of fastener. These screws place the external peltier's (test piece peltier 215) positive side 201, which is bonded to the test piece surface 51 with thermal grease 260, in compression (about 150–300 psi). Thermal grease 260 may be defined, but without limitation, as a grease that provides a thermal conductive path and allows the option of disassembly. Examples of thermal grease 260 include metal-oxide-filled synthetic grease, silicone based thermal grease, phase change thermal interface material, thermal joint compound, and the like. The preferred thermal grease 260 is Zinc-Oxide/Silicon based grease or paste. The preferred thermal grease 260 is about 60% to about 80% zinc oxide with dimethyl polysiloxane, silicone fluid and polymethysiloxane. The preferred thermal grease 260 has a specific gravity of about 2.2, its solubility in water is negligible and has a flashpoint above 250 degrees Fahrenheit. Thermal interface material may be substituted for the thermal grease. However, it is understood that any material that can bond, bind, fasten, or the like and then allow the option of disassembly can be used.

The leads 220 of the peltiers 200 are connected to the data acquisition device 400. The negative side 202 of each peltier is maintained at a common temperature through contact with common heat sink 100. The opposing positive side 201 of each peltier 200 (reference peltier 210 and test piece 215) is in contact with the reference standard 300 and the test piece 50 respectively. A difference in temperatures between the reference standard 300 and the test piece 50 will generate a differing electrical current from each peltier 200. This output is recorded and compared (reference vs. test piece) by the data acquisition device 400. An increase in current from the test piece peltier 215 over the reference peltier 210 indicates a positive heat differential and the presence of corrosion.

When introducing elements of the present invention or the preferred embodiment(s) thereof, the articles "a," "an," "the," and "said" are intended to mean there are one or more of the elements. The terms "comprising," "including," and "having" are intended to be inclusive and mean that there may be additional elements other than the listed elements.

Although the present invention has been described in considerable detail with reference to certain preferred versions thereof, other versions are possible. Therefore, the spirit and scope of the appended claims should not be limited to the description of the preferred versions contained herein.

What is claimed is:

1. A non-invasive corrosion sensor, the sensor able to detect corrosion on a test piece, the non-invasive corrosion sensor comprising:

a. a heat sink;
   b. a reference peltier and a test piece peltier, each having a positive side and a negative side, each peltier communicating with the heat sink such that the negative side of each peltier is maintained at a common temperature;
   c. a reference standard, the reference standard communicating with the positive side of the peltier, the test piece communicating with the positive side of the test piece peltier; and
   d. a data acquisition device, the data acquisition device able to record and compare the differences in temperatures of the test piece and the reference standard, whereby a higher temperature in the test piece than in the reference standard indicates the presence of corrosion, the differences in temperatures of the test piece and the reference standard obtained via electrical currents in the reference peltier and the test piece peltier.

2. A non-invasive corrosion sensor, the sensor able to detect corrosion on a test piece, the non-invasive corrosion sensor comprising:

a. a heat sink;
   b. a reference peltier and a test piece peltier, each having a positive side and a negative side, each peltier communicating with the heat sink such that the negative side of each peltier is maintained at a common temperature;
   c. a reference standard, the reference standard communicating with the positive side of the peltier, the test piece communicating with the positive side of the test piece peltier;
   a. a data acquisition device, the data acquisition device able to record and compare the differences in temperatures of the test piece and the reference standard, whereby a higher temperature in the test piece than in the reference standard indicates the presence of corrosion, the differences in temperatures of the test piece and the reference standard obtained via electrical currents in the reference peltier and the test piece peltier; and
   d. an enclosure, wherein the heat sink, the reference peltier, and the reference standard are disposed within the enclosure.

3. The non-invasive corrosion sensor of claim 2, wherein the enclosure is manufactured from polycarbonate and environmentally sealed with flowable RTV silicone coating.

4. The non-invasive corrosion sensor of claim 3, wherein the test piece and the reference standard are manufactured form the same material.

5. The non-invasive corrosion sensor of claim 4, wherein the heat sink is manufactured from aluminum.

6. The non-invasive corrosion sensor of claim 5, wherein the reference standard is polished to remove all surface corrosion and contaminates and is sealed.

7. The non-invasive corrosion sensor of claim 6, wherein each negative side of each peltier is bonded to the heat sink with thermal epoxy.

8. The non-invasive corrosion sensor of claim 7, wherein the thermal epoxy is a Zinc-Oxide/Silicon based grease.

9. The non-invasive corrosion sensor of claim 8, wherein the thermal grease is about 60 to about 80% zinc oxide with dimetyl polysiloxane, silicone fluid and polymethysiloxane.

10. The non-invasive corrosion sensor of claim 9, wherein the thermal grease has a specific gravity of about 2.2, its solubility in water is negligible and has a flashpoint above 250 degrees Fahrenheit.

11. The non-invasive corrosion sensor of claim 10, wherein the positive side of the reference peltier is bonded to the reference standard with thermal interface material.

* * * * *

UNITED STATES PATENT AND TRADEMARK OFFICE
CERTIFICATE OF CORRECTION

PATENT NO. : 6,902,316 B1
DATED : June 7, 2005
INVENTOR(S) : Pierce et al.

It is certified that error appears in the above-identified patent and that said Letters Patent is hereby corrected as shown below:

Title page,
Item [57], ABSTRACT,
Line 9, should read -- the data acquisition device is able to record and compare the --.

Column 4,
Lines 16 and 38, should read -- c. a reference standard, the reference standard communicating with the positive side of the reference peltier, the test piece communicating with the positive side of the test piece peltier; --.

Signed and Sealed this

Twenty-third Day of August, 2005

JON W. DUDAS
*Director of the United States Patent and Trademark Office*